United States Patent [19]

Cox et al.

[11] Patent Number: 5,190,871
[45] Date of Patent: Mar. 2, 1993

[54] USE OF THE SITE-SPECIFIC INTEGRATING FUNCTION OF PHAGE φC31

[75] Inventors: Karen L. Cox, Martinsville; Stuart A. Kuhstoss, Indianapolis; R. Nagaraja Rao, Indianapolis; Mark A. Richardson, Indianapolis; Brigitte E. Schoner, Monrovia; Eugene T. Seno, Indianapolis, all of Ind.

[73] Assignee: Eli Lilly and Company, Indianapolis, Ind.

[21] Appl. No.: 364,959

[22] Filed: Jun. 12, 1989

[51] Int. Cl.⁵ .................. C12N 15/74; C12N 1/21; C12N 15/09; C12N 15/63
[52] U.S. Cl. .................. 435/172.3; 435/252.35; 435/320.1
[58] Field of Search ............ 435/69.1, 252.35, 320.1, 435/172.3; 935/31, 24, 58, 60

[56] References Cited

FOREIGN PATENT DOCUMENTS 0174096 3/1986 European Pat. Off. ......... 435/172.3
0191643 8/1986 European Pat. Off. ............. 536/27

OTHER PUBLICATIONS

Balakrishnan and Backman, Gene 67:97–103 (1988).
Pernodet et al., Mol. Gen. Genet. 198:35–41 (1984).
Kuhstoss et al., J. Bact. 171:16–23 (1989).
Rodicio et al., Gene 34:283–292 (1985).
Suarez and Chater, Nature 286:527–529 (1980).
Chater et al., Gene 15:249–256 (1981).
Ow and Ausubel, J. Bact. 155:704–713 (1983).
Boccard et al., Mol. Gen. Genet. 212:432–439 (1988).
Omer and Cohen, Mol. Gen. Genet. 196:429–438 (1984).
Omer and Cohen, J. Bact. 166:999–1006 (1986).
Ramaswamy et al. Gene 67:97 (1988).
Harris et al. Gene 22:167 (1983).
Epp et al. Biol. Actinomycetes '88 (82–85) Abstract 1988.
Pouwels et al., Cloning Vectors, Elsevier Sci. Pub. (1985).
Charles et al. Gene 19(1):21 (1982).
Jones et al. Abstr. Annu. Meet. Am. Soc. Microbiol. (84:101) (1984 Abstract).
Cox et al. Lilly Research Labs J Nat Prod. (49, 6, 971–80). 1986 Abstract.
Blatz et al. Lilly Res. Lab. (32, 6, Meet., 55–64) 1986. Abstract.

Primary Examiner—Richard A. Schwartz
Assistant Examiner—John LeGuyader
Attorney, Agent, or Firm—Amy E. Hamilton; Leroy Whitaker

[57] ABSTRACT

The present invention provides a method for transforming an actinomycete with an integrating vector which has the advantages of high transformation rates into a broad host range, site-specific integration, and stable maintenance without antibiotic selection. Also provided are methods for the increased production of antibiotics and for the production of hybrid antibiotics.

28 Claims, 7 Drawing Sheets

USE OF THE SITE-SPECIFIC INTEGRATING FUNCTION OF PHAGE φC31

SUMMARY OF THE INVENTION

The in vivo amplification of genes coding for proteins involved in the biosynthesis of antibiotics can serve to increase production of that antibiotic. In actinomycetes, the usual route to this amplification has been via autonomously replicating plasmids. For reviews of Streptomyces cloning systems, see Hopwood et al., in 153 *Methods in Enzymology* 116 (1987) and Hopwood et al., in 9 *The Bacteria* 159 (1986). The present invention provides methods for increasing a given gene dosage and for adding heterologous genes that lead to the formation of new products such as hybrid antibiotics. The procedures of the present invention have many advantages over methods involving autonomously replicating plasmids.

Plasmids comprising the site-specific integrating function of phage φC31 can be used to permanently integrate copies of the gene of choice into the chromosome of many different hosts. The vectors can transform these hosts at a very high efficiency. Because some of the vectors do not have actinomycete origins of replication, the plasmids cannot exist as autonomously replicating vectors in actinomycete hosts. The plasmids only exist in their integrated form in these hosts. The integrated form is extremely stable which allows the gene copies to be maintained without antibiotic selective pressure. The result is highly beneficial in terms of cost, efficiency, and stability of the fermentation process.

The integrating vectors can be used to integrate genes which increase the yield of known products or generate novel products, such as hybrid antibiotics or other novel secondary metabolites. The vector can also be used to integrate antibiotic resistance genes into strains in order to carry out bioconversions with compounds to which the strain is normally sensitive. The resulting transformed hosts and methods of making the antibiotics are within the scope of the present invention.

DETAILED DESCRIPTION OF THE INVENTION

The present invention represents a significant advance in the introduction and maintenance of cloned genes in the antibiotic producing streptomycetes and related organisms. The invention is based on the use of an ~2 kb fragment of actinophage φC31 (Chater et al., Gene 19:21-32 (1982). A vector which comprises this fragment, plasmid pKC796, is available from the NRRL (Northern Regional Research Laboratories, Peoria, Illinois 61604) under the accession number B-18477. The plasmid has been deposited in accordance with the terms of the Budapest Treaty. See FIG. 1 for a restriction map of pKC796.

For purposes of the present invention as disclosed and claimed herein, the following terms are as defined below.

Antibiotic—a substance produced by a microorganism that, either naturally or with limited chemical modification, inhibits the growth of or kills another microorganism or eukaryotic cell.

Antibiotic Biosynthetic Gene—a DNA segment that encodes an enzymatic activity or encodes a product that regulates expression of an enzymatic activity that is necessary for an enzymatic reaction in the process of converting primary metabolites to antibiotic intermediates, which can also possess antibiotic activity, and then to antibiotics.

Antibiotic Biosynthetic Pathway—the set of antibiotic biosynthetic genes and biochemical reactions necessary for the process of converting primary metabolites to antibiotic intermediates and then to antibiotics.

Antibiotic-Producing Microorganism—any organism, including, but not limited to Actinoplanes, Actinomadura, Bacillus, Cephalosporium, Micromonospora, Penicillium, Nocardia, and Streptomyces, that either produces an antibiotic or contains genes that, if expressed, would produce an antibiotic.

Antibiotic Resistance-Conferring Gene—a DNA segment that encodes an activity that confers resistance to an antibiotic.

AmR—the apramycin-resistant phenotype or gene conferring same.

ApR—the ampicillin-resistant phenotype or gene conferring same.

attP—the attachment site of phage φC31 for integration into the host chromosome.

cos site—the lambda cohesive end sequence.

Host Cell—an organism, including the viable protoplast thereof, that can be transformed with a recombinant DNA cloning vector.

Hybrid Antibiotic—an antibiotic produced when a heterologous antibiotic biosynthetic gene is introduced into an antibiotic producing microorganism, said antibiotic biosynthetic gene encoding an enzyme that is capable of modifying the antibiotic produced by the original host cell.

Integrating Vector—a vector which, when transformed into a host cell, does not autonomously replicate within the host cell but rather integrates into the host chromosome by recombination.

ori—as used in the Figures herein, an *E. coli* origin of replication.

Recombinant DNA Cloning Vector—any selectable and autonomously replicating or chromosomally integrating agent, including but not limited to plasmids and phages, comprising a DNA molecule to which additional DNA can be or has been added.

rep—as used in the Figures herein, a Streptomyces plasmid origin of replication.

Restriction Fragment—any linear DNA generated by the action of one or more restriction enzymes.

Sensitive Host Cell—a host cell, including the viable protoplast thereof, that cannot grow in the presence of a given antibiotic without a DNA segment that confers resistance thereto.

Site-specific integration—the process of integration by a vector into the host chromosome that utilizes specific bacterial (attB) and plasmid or phage (attP) attachment sites and specific recombinational systems (int) coded by plasmid or phage.

Transformant—a recipient host cell, including the viable protoplast thereof, that has undergone transformation.

Transformation—the introduction of DNA into a recipient host cell, including the viable protoplast thereof, and subsequent maintenance of said DNA that results in a change in the genotype of the recipient cell.

tsr—the thiostrepton-resistant phenotype or gene conferring same.

DESCRIPTION OF THE FIGURES

The restriction site and function maps presented in the Figures are approximate representations of the recombinant DNA vector discussed herein. The spacing of restriction sites on the map is proportional to the actual spacing of the restriction sites on the vector, but observed restriction site distances may vary somewhat from calculated map distances. The maps do not necessarily provide an exhaustive listing of all the cut sites of a given restriction enzyme; therefore, there may be more restriction sites of a given type on the vector than actually shown on the map.

Figure 1:
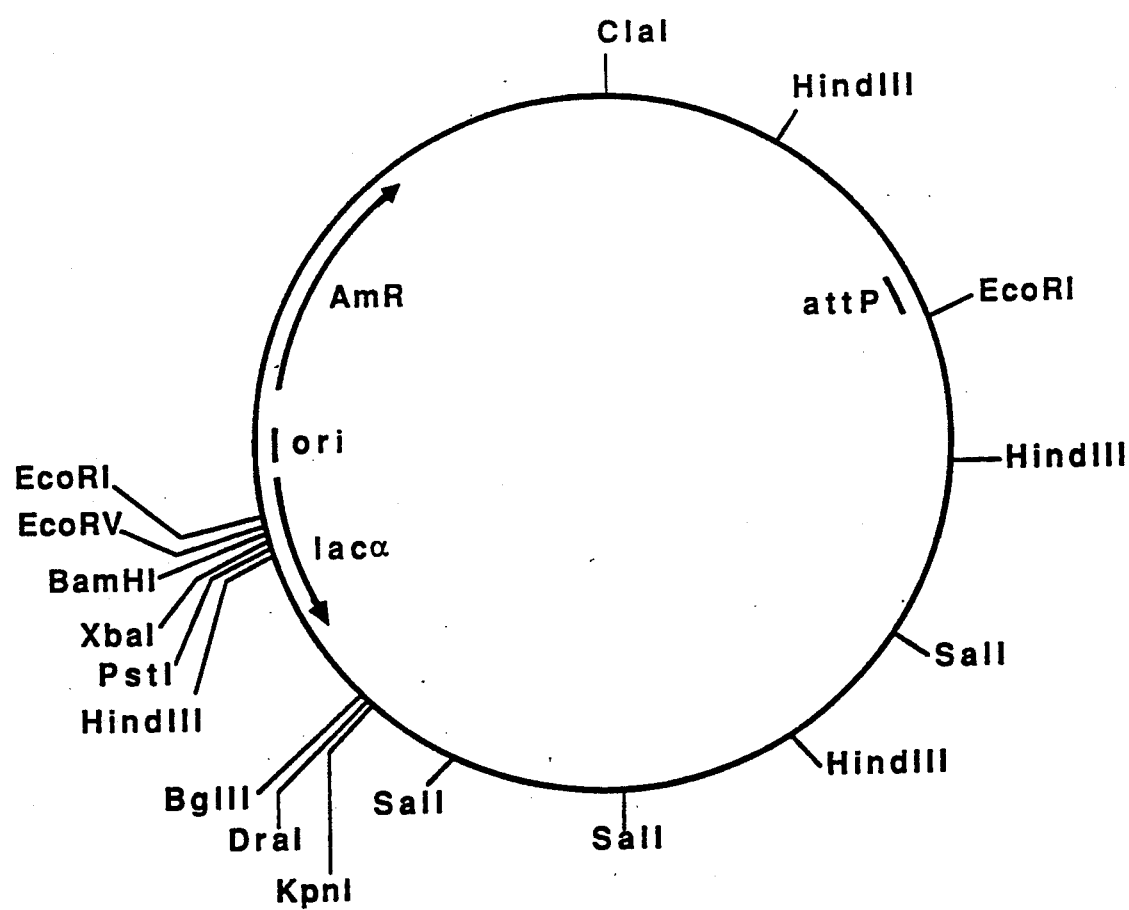
FIG. 1 - Restriction Site and Function Map of Plasmid pKC796.

The present invention provides plasmid vectors which comprise the site-specific integrating function of the actinomycete phage φC31. The DNA sequence of this region, presented below, was unknown prior to the present invention. Only one strand of the sequence is shown, reading in the 5'→3'0 direction.

```
   1 CGTCCCGTAC AACGTCGCGC GTGAGCGGGT CGGTTCCGGT GAAGAGATAC
  51 AGGGTCATGG AACGCGCGCT ACAGCGCCGG AAAAACGGAA CCTGGGTCGT
 101 GCGCAAGAAT CCGCCGTTCG TGATCTTCGA TGAAGTCATG GGCGATTACT
 151 GCGCGCTGCC CCAGGACGAC GACGGCGAGC CGGTGACGCT CGAATGGCGT
 201 TCGCGGTCGG CGGCGTATGA CTGGCTCGCC CACTGCCTTC AGACGTGGCA
 251 GATGTGGGAG CGCACGGGGC GAGCCGCTGA CGTCCCGAAG GCGTGGCGCG
                                     AatII
 301 GCTTCCCCGT GCCGGAGCAA TCGCCCTGGG TGGGTTACAC GACGCCCCTC
 351 TATGGCCCGT ACTGACGGAC ACACCGAAGC CCCGGCGGCA ACCCTCAGCG
 401 GATGCCCCGG GGCTTCACGT TTTCCCAGGT CAGAAGCGGT TTTCGGGAGT
 451 AGTGCCCCAA CTGGGGTAAC CTTTGAGTTC TCTCAGTTGG GGGCGTAGGG
 501 TCGCCGACAT GACACAAGGG GTTGTGACCG GGGTGGACAC GTACGCGGGT
 551 GCTTACGACC GTCAGTCGCG CGAGCGCGAG AATTCGAGCG CAGCAAGCCC
 601 AGCGACACAG CGTAGCGCCA ACGAAGACAA GGCGGCCGAC CTTCAGCGCG
 651 AAGTCGAGCG CGACGGGGGC CGGTTCAGGT TCGTCGGGCA TTTCAGCGAA
 701 GCGCCGGGCA CGTCGGCGTT CGGGACGGCG GAGCGCCCGG AGTTCGAACG
 751 CATCCTGAAC GAATGCCGCG CCGGGCGGCT CAACATGATC ATTGTCTATG
 801 ACGTGTCGCG CTTCTCGCGC CTGAAGGTCA TGGACGCGAT TCCGATTGTC
 851 TCGGAATTGC TCGCCCTGGG CGTGACGATT GTTTCCACTC AGGAAGGCGT
 901 CTTCCGGCAG GGAAACGTCA TGGACCTGAT TCACCTGATT ATGCGGCTCG
 951 ACGCGTCGCA CAAAGAATCT TCGCTGAAGT CGGCGAAGAT TCTCGACACG
1001 AAGAACCTTC AGCGCGAATT GGGCGGGTAC GTCGGCGGGA AGGCGCCTTA
1051 CGGCTTCGAG CTTGTTTCGG AGACGAAGGA GATCACGCGC AACGGCCGAA
1101 TGGTCAATGT CGTCATCAAC AAGCTTGCGC ACTCGACCAC TCCCCTTACC
1151 GGACCCTTCG AGTTCGAGCC CGACGTAATC CGGTGGTGGT GGCGTGAGAT
1201 CAAGACGCAC AAACACCTTC CCTTCAAGCC GGGCAGTCAA GCCGCCATTC
1251 ACCCGGGCAG CATCACGGGG CTTTGTAAGC GCATGGACGC TGACGCCGTG
1301 CCGACCCGGG GCGAGACGAT TGGGAAGAAG ACCGCTTCAA GCGCCTGGGA
1351 CCCGGCAACC GTTATGCGAA TCCTTCGGGA CCCGCGTATT GCGGGCTTCG
1401 CCGCTGAGGT GATCTACAAG AAGAAGCCGG ACGGCACGCC GACCACGAAG
1451 ATTGAGGGTT ACCGCATTCA GCGCGACCCG ATCACGCTCC GGCCGGTCGA
1501 GCTTGATTGC GGACCGATCA TCGAGCCCGC TGAGTGGTAT GAGCTTCAGG
1551 CGTGGTTGGA CGGCAGGGGG CGCGGCAAGG GGCTTTCCCG GGGGCAAGCC
1601 ATTCTGTCCG CCATGGACAA GCTGTACTGC GAGTGTGGCG CCGTCATGAC
1651 TTCGAAGCGC GGGGAAGAAT CGATCAAGGA CTCTTACCGC TGCCGTCGCC
1701 GGAAGGTGGT CGACCCGTCC GCACCTGGGC AGCACGAAGG CACGTGCAAC
1751 GTCAGCATGG CGGCACTCGA CAAGTTCGTT GCGGAACGCA TCTTCAACAA
1801 GATCAGGCAC GCCGAAGGCG ACGAAGAGAC GTTGGCGCTT CTGTGGGAAG
1851 CCGCCCGACG CTTCGGCAAG CTCACTGAGG CGCCTGAGAA GAGCGGCGAA
1901 CGGGCGAACC TTGTTGCGGA GCGCGCCGAC GCCCTGAACG CCCTTGAAGA
1951 GCTGTACGAA GACCGCGCGG CAGGCGCGTA CGACGGACCC GTTGGCAGGA
2001 AGCACTTCCG GAAGCAACAG GCAGCGCTGA CGCTCCGGCA GCAAGGGGCG
2051 GAAGAGCGGC TTGCCGAACT TGAAGCCCGA GAAGCCCCGA AGCTTCCCCT
2101 TGACCAATGG TTCCCCGAAG ACGCCGACGC TGACCCGACC GGCCCTAAGT
2151 CGTGGTGGGG GCGCGCGTCA GTAGACGACA AGCGCGTGTT CGTCGGGCTC
2201 TTCGTAGACA AGATCGTTGT CACGAAGTCG ACTACGGGCA GGGGGCAGGG
2251 AACGCCCATC GAGAAGCGCG CTTCGATCAC GTGGGCGAAG CCGCCGACCG
2301 ACGACGACGA AGACGACGCC CAGGACGGCA CAGGACGGCA AGCGGCGTAG
2351 CGAGACACCC GGGAAGCCTG TTAGGCGCTG AGACGGGCGC ACAGCGGGCT
2401 TCCTGGGGCA GCGGGAAGGG TCGGCCGGTC CCCCGGTCGG CCCATTTCTC
2451 TTGTCTCGGT TTAGTTAGTT AGCCTAAGTA ACAGTGACTC CGTCACCACA
2501 GCACAGCGGA GCGAGCCGTT GACCTGGGGG AAGTGATGCT GTGACGGAAT
2551 GACTCGAAAC ACACATTCCT AATGACTTCT CATTGGGTAA TCCAGACTTC
2601 ACGTCCACTT CATCACAGCG TCACCCGGGC GCCCTTCGCT GTGACCCCGA
2651 ATCAGGTTGC CGACAACCTT CATATAGGTA GAGGGGTTTA CGCGCCACGC
2701 ATCAAGCACC GCTAAGGAAC GGCGTCGAGC GCTACCCACT CAGGCCGGTC
2751 ACTCCCCTGA TCTCTCCCAG GGTTGAGCGA CCGGCGTTGC CTCCCTAGCT
2801 CAGTTCGGTT AGAGCGCCTG TTTCGTAATC AGGGGGTCGG CGGTTCGAAT
2851 CCGTCGGGGG GCTCAATGAG CGGATACACA ATCGCTTGGC TCGCATGGCT
2901 TGCCGCGTTC GGCGTCATTG AGGGTCGAGC GCTCTTCAAT AAGAAGCCGG
2951 GCGACACGCT GAGCGAACAC GTCTGGTCAT GGTTCGCCAC GCAAAGCGGC
```

```
-continued
3001 AGTACAGGCA  AGCCTTCGGG  TTGGGTGCGT  GCTCGACGCT  TTGCGCTACT
3051 GGCCTTCATG  GGTTGGCTCA  CTGCCCACTT  CATGACGGGC  GGTCGCTTCT
3101 AGCXCTGCCG  CGCCCAGCCT  ACTCACGTGA  GTAGGTAGGG  GGGTGTCGAC
2151 GGATAGGGGG  GTGTCCCCGG  AAGGGGGGGG  GGGGTGCCCT  ATGCGTACCC
3201 GGTGTCTCGA  CTGTAGGGAC  TGGGCTACTC  ATGGTGGGCG  CTGTGCTCAG
3251 CACCACGCCA  CCTATCAGGC  ACAGCGCAGT  GTGAAGAGCC  ATGCGAAGCG
3301 GCGTGCTGCT  ATCGCCCGTG  GGAACAACGC  TGCGGCGAAG  ATGCGTCGTG
3351 CTATCCGTAA  GGCAGTGGGC  GCGCACTGTG  CTACCTGCCT  GGGTTGGTAC
3401 C
``` wherein A is a deoxyadenyl residue, G is a deoxyguanyl residue, C is a deoxycytidyl residue, T is a thymidyl residue, and X is a deoxyadenyl, deoxycytidyl, deoxyguanyl or thymidyl residue.

The DNA sequence comprising all the elements of DNA required for site-specific integration is bounded by the AatII restriction site (underlined) beginning at position 279 and the underlined thymidyl nucleotide at position 2369 of the above sequence. Plasmids comprising this sequence transform actinomycetes at extremely high rates. The plasmids are superior to phage cloning vectors comprising this sequence (Suarez, J.E. and Chater, K.F., Nature 286:527–529 (1980)) in that there is less limitation on the amount of DNA which can be cloned into the plasmid. The cloning capacity of phage vectors is limited to the amount of DNA which can be packaged.

Those skilled in the art will readily recognize that the variety of vectors which can be created that comprise this fragment is virtually limitless. The only absolute requirement is that the plasmid comprise an origin of replication which functions in the host cell in which constructions are made, such as $E.\ coli$ or $Bacillus$. No actinomycete origin of replication is required. In fact, a preferred plasmid comprising the $\phi$C31 fragment comprises no actinomycete origin of replication. Other features, such as an antibiotic resistance gene, a multiple cloning site and cos site are useful but not required. A description of the generation and uses of cosmid shuttle vectors can be found in Rao et al., 1987, in $Methods\ in\ Enzymology$, 153:166–198 (R.Wu and L. Grossman, eds. Academic Press, NY). In short, any plasmid which comprises the $\phi$C31 fragment and which does not direct the formation of phage plaques is within the scope of this invention.

A preferred embodiment of the present invention is plasmid pKC796 (see FIG. 1). The plasmid has an $E.\ coli$ origin of replication derived from the pUC plasmids (available from Bethesda Research Laboratories, Inc., P.O. Box 577, Gaithersburg, MD 20760) which facilitates plasmid construction. Because plasmid construction in $E.\ coli$ is so simple and quick compared to constructions carried out in Streptomyces, it is advantageous that all the initial steps can be carried out in $E.\ coli$. Only the final product is then transformed into Streptomyces for use in antibiotic production.

The vector has no Streptomyces origin of replication, which is a great advantage in an integrating vector. Multiple origins of replication in a chromosome can lead to instability of the construction. Experiments have shown that transformation rates for vectors with a Streptomyces origin of replication and an integrating function are far lower than transformation rates for vectors with either function alone. This result may be due to the instability problem.

Plasmid pKC796 also comprises the attachment site (attP) of Streptomyces phage $\phi$C31. Chater et al., Gene 19: 21-32 (1982). The site is on an ~4 kb ClaI-KpnI fragment derived from $\phi$C31. The protein(s) recognizing the attP and attB site direct site-specific integration into the chromosome. Once integrated, the construction is extraordinarily stable with virtually no reversion to the natural state. The site-specific nature of the integration facilitates analysis of the integrants.

Plasmid pKC796 also comprises the apramycin resistance gene, which is conveniently selectable in both $E.\ coli$ and Streptomyces. The apramycin selection during the transformation process in Streptomyces ensures that integration has occurred due to the fact that there is no Streptomyces origin of replication on the vector. The apramycin selection can then be removed without fear of loss of the desired phenotype, as the integrated DNA is stable.

The vector comprises a multiple cloning site within the lac$\alpha$($\beta$-galactosidase) gene. See FIG. 1 for the available cloning sites. An $E.\ coli$ transformant carrying the pKC796 plasmid with an insert is easily detected as a white colony (as opposed to blue) when grown on media containing Xgal (5-bromo-4-chloro-3-indolyl-$\beta$-D-galactoside) and IPTG (isopropyl-$\beta$-D-thiogalactoside).

One of the most important assets of the present invention is the vectors' ability to transform many actinomycete strains at very high rates. The following table shows the results of some representative transformations with plasmid pKC796.

TABLE I

| Strain | Approximate Transformation Frequency (per $\mu$g DNA) |
|---|---|
| S. ambofaciens | $\geq 10^6$ |
| S. griseofuscus | $\geq 10^6$ |
| S. lividans | $\geq 10^6$ |
| S. lipmanii | $\geq 10^4$ |
| S. fradiae | $\geq 10^3$ |
| S. thermotolerans | $\geq 10^3$ |
| Amycolatopsis orientalis | $\geq 10^2$ |

The following tables provide a non-exhaustive list of antibiotic-producing microorganisms to which the present invention may be applied. The invention, in some instances, may also be used to generate increased amounts of products or novel products other than antibiotics.

TABLE II

| Aminocyclitol Antibiotic-Producing Organisms | |
|---|---|
| Organism | Antibiotic |
| *Bacillus* | |
| various species | various aminocyclitols |
| *Micromonospora* | |
| various species | gentamycins |
| *Saccharopolyspora* | |
| various species | various aminocyclitols |
| *Streptomyces* | |
| albogriseolus | neomycins |
| albus var. metamycinus | metamycin |
| aquacanus | N-methyl hygromycin B |
| atrofaciens | hygromycins |

TABLE II-continued
Aminocyclitol Antibiotic-Producing Organisms

| Organism | Antibiotic |
| --- | --- |
| bikiniensis | streptomycin |
| bluensis var. bluensis | bluensomycin |
| canus | ribosyl paromamine |
| catenulae | catenulin |
| chrestomyceticus | aminosidine |
| crystallinus | hygromycin A |
| erythrochromogenes var. narutoensis | streptomycin |
| eurocidicus | A16316-C |
| fradiae | hybrimycins and neomycins |
| fradiae var. italicus | aminosidine |
| galbus | streptomycin |
| griseus | streptomycin |
| griseoflavus | MA 1267 |
| hofuensis | seldomycin complex |
| hygroscopicus | hygromycins, leucanicidin, and hygrolidin |
| hygroscopicus forma glebosus | glebomycin |
| hygroscopicus var. limoneus | validamycins |
| hygroscopicus var. sagamiensis | spectinomycin |
| kanamyceticus | kanamycin A and B |
| kasugaensis | kasugamycins |
| kasugaspinus | kasugamycins |
| lavendulae | neomycin |
| lividus | lividomycins |
| mashuensis | streptomycin |
| microsporeus | SF-767 |
| netropsis | LL-AM31 |
| noboritoensis | hygromycins |
| olivaceus | streptomycin |
| olivoreticuli var. cellulophilus | destomycin A |
| poolensis | streptomycin |
| rameus | streptomycin |
| ribosidificus | SF733 |
| rimofaciens | destomycin A |
| rimosus forma paromomycinus | paromomycins and catenulin |
| spectabilis | spectinomycin |
| tenebrarius | tobramycin and apramycin |
| *Streptoverticillium* | |
| flavopersicus | spectinomycin |

TABLE III
Ansamycin Antibiotic-Producing Organisms

| Organism | Antibiotic |
| --- | --- |
| *Micromonospora* | |
| various species | various ansamycins |
| *Nocardia* | |
| mediterranei | rifamycin |
| *Streptomyces* | |
| collinus | ansatrienes and napthomycins |
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotrienes |
| sp. E88 | mycotrienes |
| spectabilis | streptovaricins |
| tolypophorous | tolypomycin |

TABLE IV
Anthracycline and Quinone Antibiotic-Producing Organisms

| Organism | Antibiotic |
| --- | --- |
| *Streptomyces* | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromogenes | arugomycin |

TABLE V
β-Lactam Antibiotic-Producing Organisms

| Organism | Antibiotic |
| --- | --- |
| *Nocardia* | |
| lactamadurans | cephamycin C |
| uniformis | nocardicin |
| *Streptomyces* | |
| antibioticus | clavulanic acid |
| argenteolus | asparenomycin A, MM 4550, and MM 13902 |
| cattleya | thienamycin |
| chartreusis | SF 1623 and cephamycin A and B |
| *Streptomyces* | |
| cinnamonensis | cephamycin A and B |
| clavuligerus | PA-32413-I, cephamycin C, A16886A, penicillins cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxycephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| rochei | cephamycin A and B |
| sioyaensis | MM 4550 and MM 13902 |
| sp. OA-6129 | OA-6129A |
| sp. KC-6643 | carpetimycin A |
| viridochromogenes | cephamycin A and B |
| wadayamensis | WS-3442-D |

TABLE VI
Macrolide, Lincosamide, and Streptogramin Antibiotic-Producing Organisms

| Organism | Antibiotic |
| --- | --- |
| *Micromonospora* | |
| rosaria | rosaramicin |
| *Saccharopolyspora* | |
| erythraea | erythromycins |
| *Streptomyces* | |
| albireticuli | carbomycin |
| albogriseolus | mikonomycin |
| albus | albomycetin |
| albus var. coilmyceticus | coleimycin |
| ambofaciens | spiramycin and |

TABLE VI-continued
Macrolide, Lincosamide, and Streptogramin Antibiotic-Producing Organisms

| Organism | Antibiotic |
|---|---|
| | foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin A$_3$ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin A$_3$ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE VII
Miscellaneous Antibiotic-Producing Streptomyces

| Antibiotic Type | Streptomyces Species | Antibiotic |
|---|---|---|
| amino acid analogues | sp. | cycloserine |
| cyclopentane ring-containing | coelicolor | methylenomycin A |
| | erythrochromogenes | sarkomycin |
| | kasugaensis | aureothricin and thiolutin |
| | violaceoruber | methylenomycin A |

TABLE VII-continued
Miscellaneous Antibiotic-Producing Streptomyces

| Antibiotic Type | Streptomyces Species | Antibiotic |
|---|---|---|
| nitro-containing polyenes | venezuelae | chloramphenicol |
| | griseus | candicidin |
| | nodosus | amphotericin B |
| | noursei | nystatin |
| tetracyclines | aureofaciens | tetracycline, chlortetracycline, demethyltetracycline, and demethylchlortetracycline |
| | rimosus | oxytetracycline |

TABLE VIII
Nucleoside Antibiotic-Producing Organisms

| Organism | Antibiotic |
|---|---|
| Corynebacterium | |
| michiganese pv. rathayi | tunicamycin analogues |
| Nocardia | |
| candidus | pyrazofurin |
| Streptomyces | |
| antibioticus | ara-A |
| chartreusis | tunicamycin |
| griseoflavus var. thuringiensis | streptoviridans |
| griseolus | sinefungin |
| lysosuperificus | tunicamycin |

TABLE IX
Peptide Antibiotic-Producing Organisms

| Organism | Antibiotic |
|---|---|
| Actinoplanes | |
| missouriensis | actaplanin |
| teichomyceticus | teicoplanin |
| Nocardia | |
| candidus | A-35512 and avoparcin |
| lurida | ristocetin |
| orientalis | vancomycin |
| Streptomyces | |
| antibioticus | actinomycin |
| aureus | thiostrepton |
| canus | amphomycin |
| eburosporeus | LL-AM374 |
| haranomachiensis | vancomycin |
| pristinaespiralis | pristinamycin |
| roseosporus | lipopeptides, such as A21978C |
| toyocaensis | A47934 |
| virginiae | A41030 |

TABLE X
Polyether Antibiotic-Producing Organism

| Organism | Antibiotic |
|---|---|
| Actinomadura | |
| various species | various polyethers |
| oligosporus | A80190 |
| Dactylosporangium | |
| various species | various polyethers |
| Nocardia | |
| various species | various polyethers |
| Streptomyces | |
| albus | A204, A28695A and B, and salinomycin |
| aureofaciens | narasin |
| bobili | A80438 |
| cacaoi var. asoensis | lysocellin |
| chartreusis | A23187 |
| cinnamonensis | monensin |
| conglobatus | ionomycin |

TABLE X-continued

| Polyether Antibiotic-Producing Organism | |
|---|---|
| Organism | Antibiotic |
| eurocidicus var. asterocidicus | laidlomycin |
| flaveolus | CP38936 |
| gallinarius | RP 30504 |
| griseus | grisorixin |
| hygroscopicus | A218, emericid, DE3936, A120A, A28695A and B, etheromycin, and dianemycin |
| lasaliensis | lasalocid |
| longwoodensis | lysocellin |
| mutabilis | S-11743a |
| pactum | A80438 |
| ribosidificus | Ionomycin |
| violaceoniger | nigericin |
| Streptoverticillium various species | polyethers |

If it is desired to create integrating vectors with features other than those of pKC796, the φC31 fragment may be obtained from plasmid pKC796, deposited with the NRRL under accession number NRRL B-18477 by a combination of site-specific mutagenesis and restriction enzyme digestion. First, the plasmid may be site-specifically mutagenized in accordance with the method of Adelman et al., DNA 2:183–193 (1983), herein incorporated by reference, using the synthetic DNA fragment TGTTAGGCGCTGAGACGGGC-CCACAGCGGGCTTCCTGGGGC. Incorporating this fragment into the plasmid generates the restriction site ApaI at the 3' end of the fragment. The fragment can then be isolated as a AatII-ApaI restriction fragment. In some contexts it may be necessary to insert a promoter functional in actinomycetes at the AatII site. Such promoters are well-known to one skilled in the art. One skilled in the art may then insert the fragment as is into the plasmid of their choice or may adapt the ends with oligonucleotide linkers to insert the fragment at a desired restriction site. One skilled in the art will also recognize that a synthetic DNA fragment comprising any restriction site may be inserted into the plasmid using site-specific mutagenesis and the fragment subsequently isolated by digestion with that restriction enzyme.

The integrating vector of the present invention has great utility in many aspects of Streptomyces research and commercialization of Streptomyces fermentation products. Preferred uses are to integrate into the host chromosome extra copies of homologous genes or new copies of heterologous genes. The use is not limited to genes involved in antibiotic production or resistance. For example, genes involved in amino acid production could be integrated into an auxotrophic strain, which would enable the growth of the strain on media not supplemented with the particular amino acid. The salient feature of all such experiments is the subsequent maintenance of the genes without antibiotic selection.

Figure 2:
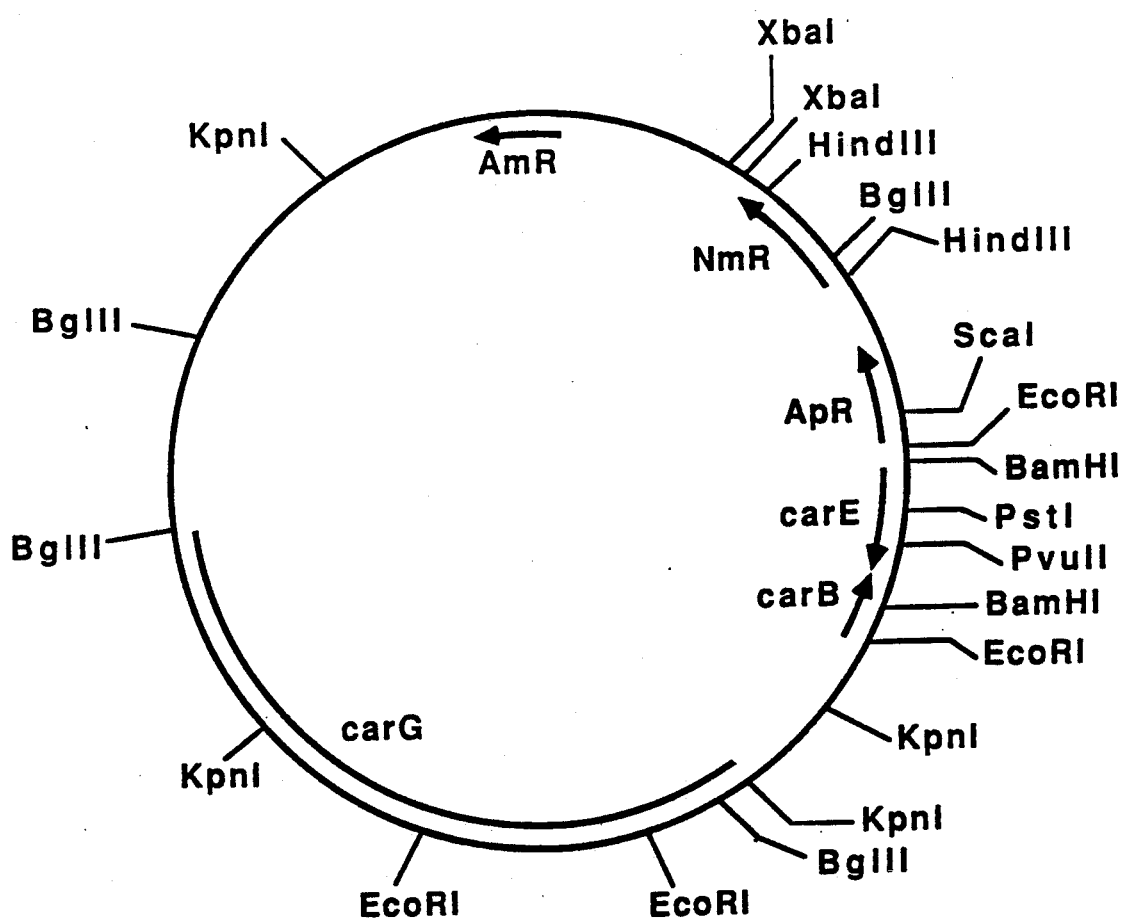
FIG. 2 - Restriction Site and Function Map of Plasmid pOJ171.

One preferred use is exemplified by the integration of the carE gene (described and claimed in U.S. Patent Application No. 07/194,672 filed May 13, 1988) of Streptomyces thermotolerans into the Streptomyces ambofaciens genome. The S. thermotolerans carE gene encodes a 4"-O-isovaleryl acylase which attaches the isovaleryl group of isovaleryl coenzyme A to a mycarose sugar residue of the macrolide antibiotic carbomycin. S. ambofaciens produces the macrolide antibiotic spiramycin and a variety of other spiramycin-related compounds that contain a mycarose residue with a 4"-OH group. S. ambofaciens does not produce a 4"-O-isovaleryl acylase activity. The carE gene can be isolated from plasmid pOJ171, which can be obtained from the NRRL in E. coli K12 SF8 under the accession number NRRL B-18169. A restriction site and function map of pOJ171 is presented in FIG. 2.

Figure 3:
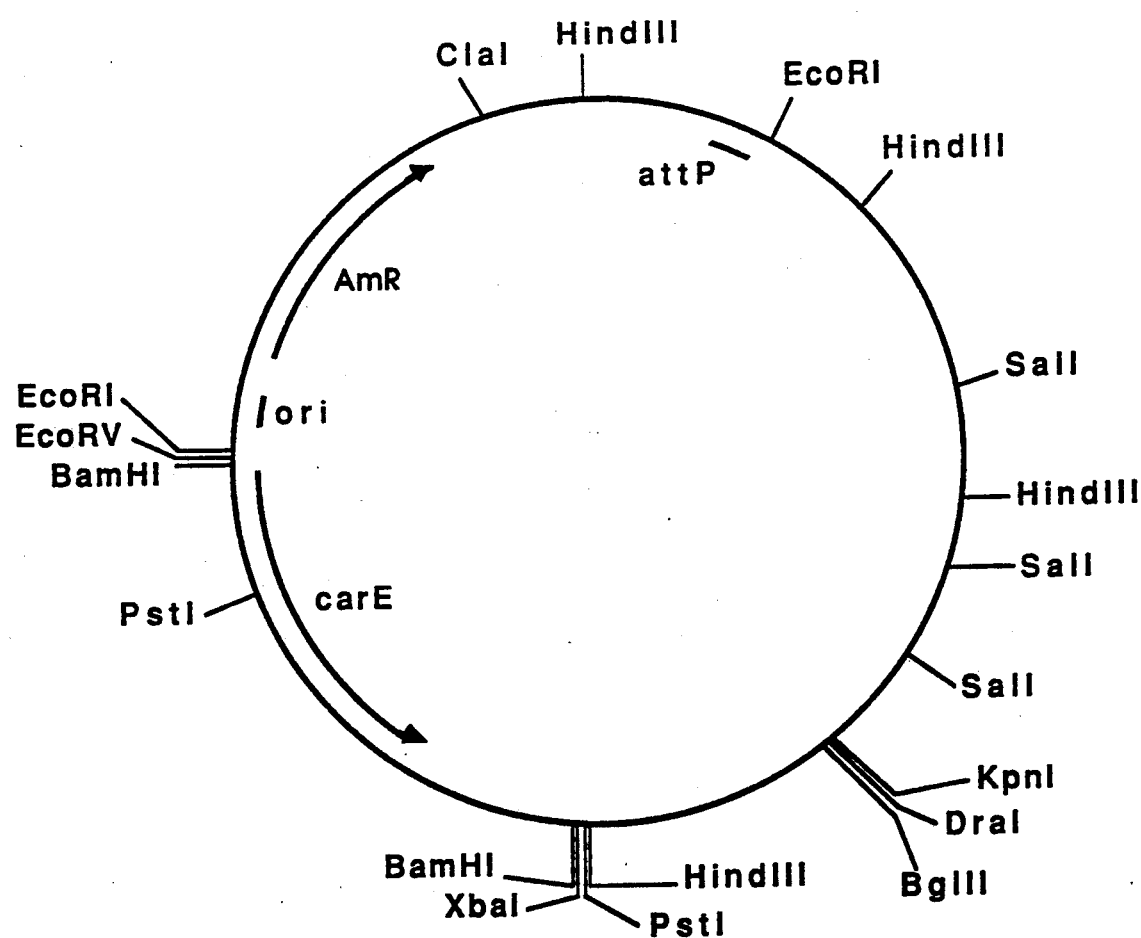
FIG. 3 - Restriction Site and Function Map of Plasmid pOJ242.
Figure 4:
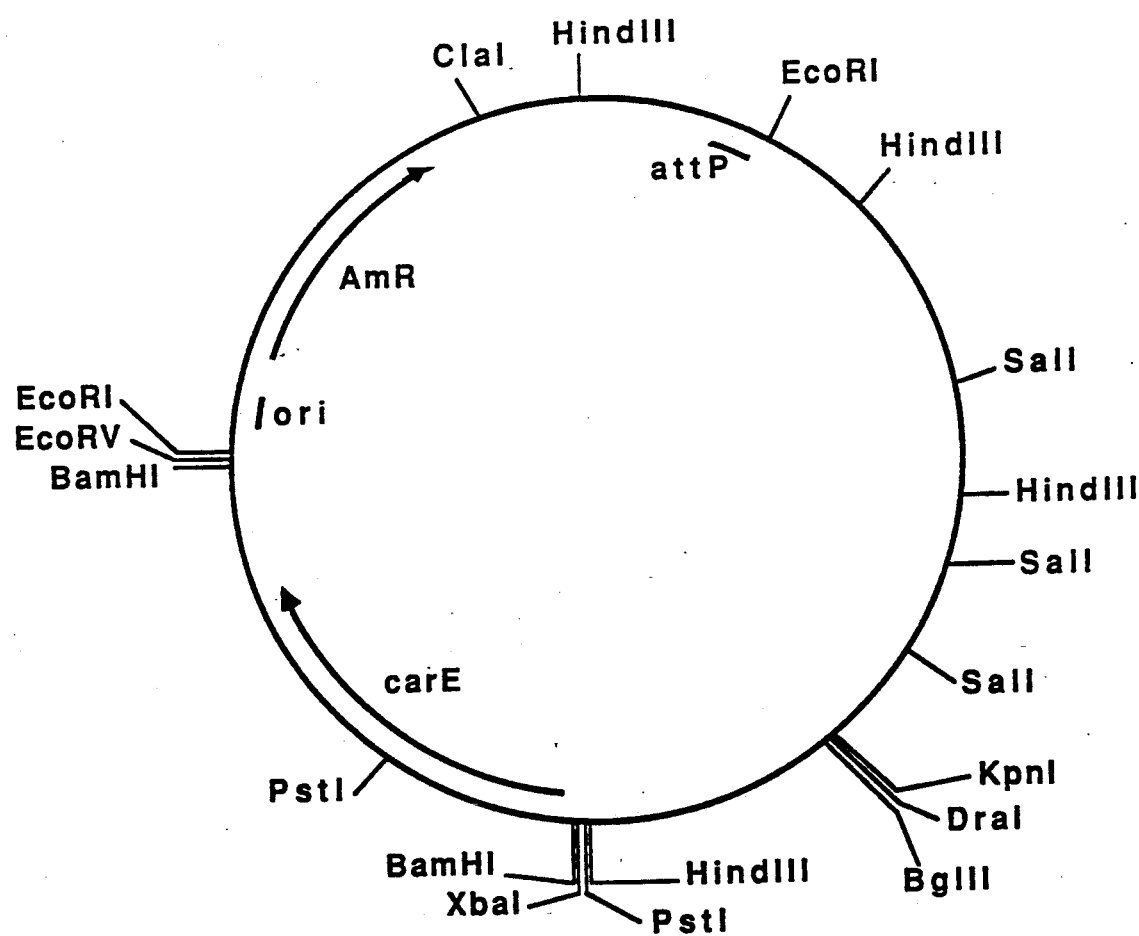
FIG. 4 - Restriction Site and Function Map of Plasmid pOJ243.

The ~2.4 kb BamHI restriction fragment isolated from plasmid pOJ171 is inserted into BamHI-digested pKC796 (NRRL B-18477). The fragment can be inserted in both orientations, yielding plasmids pOJ242 and pOJ243 (see FIGS. 3 and 4, respectively). Both plasmids and the control vector pKC796 were transformed into an S. ambofaciens strain such as NRRL 2420. Transformants were initially selected with the antibiotic apramycin. The plasmids necessarily integrate into the chromosome because no Streptomyces origins of replication are present on the vectors. Due to the stable integration, no subsequent maintenance with apramycin is required.

The presence of the carE gene in the S. ambofaciens chromosome causes the strain to produce isovaleryl spiramycin. The S. ambofaciens strains which have integrated the parent pKC796 vector continue to produce spiramycin. This method of producing isovaleryl spiramycin has two major advantages over methods involving the introduction of the carE gene on an autonomously replicating plasmid. First, the transformants can be grown without antibiotic selection, thus decreasing cost and increasing efficiency. The second advantage is that the integrated transformants produce a greater amount of isovaleryl spiramycin than replicating plasmids carrying the same gene because replicating plasmids seem to depress antibiotic production. These advantages apply generally when the integrating vector is used with any gene and are not limited to situations where the carE gene is utilized.

The present invention thus provides a method for producing hybrid antibiotics, said method comprising 1) transforming a microorganism that produces an antibiotic with a plasmid vector comprising a DNA sequence which comprises the site-specific integrating functions of phage φC31, said vector also comprising an antibiotic biosynthetic gene that codes for an enzyme or other gene product not previously expressed in said microorganism and that convert said antibiotic to an antibiotic not previously produced by said microorganism and 2) culturing said microorganism transformed with said vector under conditions suitable for producing the hybrid antibiotic.

Another preferred use of the integrating vector is to increase the production of an antibiotic by integrating the antibiotic biosynthetic gene(s) into the host chromosome via the vector. When production of the antibiotic is increased, it may also be valuable to integrate extra copies of the respective antibiotic resistance gene(s) to avoid inhibition by the antibiotic. The production of many fermentation products such as tylosin, monensin, and narasin may be improved by this method.

Integration of cloned genes using the integrating vector has numerous advantages. Stable maintenance of cloned genes in streptomycete fermentations (which involve many cell generations) in the absence of a selective agent has been a significant problem which is overcome by the present invention. For example, in tylosin production, stable maintenance of the cloned tylF gene enhances the conversion of macrocin to tylosin, providing larger quantities of tylosin. In addition to its stability, the integrative vector has a lesser inhibitory effect on antibiotic production than autonomous plasmids.

The use of the integrating vector to stably maintain cloned genes in order to increase antibiotic production is exemplified herein by using the vector and cloned tylosin biosynthetic genes to increase the production of tylosin. See Examples 3–5.

Tylosin production strains such as *Streptomyces fradiae* T1405 accumulate the tylosin precursors demethylmacrocin and macrocin. Fermentation cultures of the strain with extra copies of the tylE and tylF genes integrated into the chromosome produce increased amounts of the tylF-encoded macrocin O-methyltransferase and tylE-encoded demethylmacrocin O-methyltransferase. The result is increased conversion of demethylmacrocin to macrocin and macrocin to tylosin and thus, a greater yield of the desired end product tylosin. The tylE and tylF genes along with other tylosin biosynthetic genes were described in European Patent Publication Ser. No. 0238323, published Sep. 23, 1987.

The BamHI fragment comprising the tylF gene is derived from plasmid pHJL280 (available from the NRRL in *E. coli* K12 HB101 as NRRL B-18043; see FIG. 5). The fragment is then inserted into BamHI-digested pKC796. The resulting plasmids (differing by the orientation of the inserted BamHI fragment) are called pSKC50 and pSKC51. When transformed into the *S. fradiae* production strain T1405, the integrated vector causes tylosin production to increase to 136% as compared to the production levels of the T1405 control of 100%. The stability of the transformants is demonstrated by the fact that virtually 100% of the colony forming units retain the apramycin resistance phenotype provided by the vector after at least three passages in the absence of selection.

The ability to transform tylosin production strains is a feature not found with other site-specific integrative vectors tested. The experiment was attempted with two other Streptomyces site-specific integrating vectors lacking a Streptomyces origin of replication: pIJ4210, which is the *Streptomyces coelicolor* minicircle cloned into the *E. coli* plasmid pBR325 (Lydiate et al., Mol. Gen. Genet. 203:79–88 (1986)) and plasmids (Kuhstoss et al., J. Bact. 171:16–23 (1989)) derived from the integrative *S. ambofaciens* plasmid pSAM2 (Pernodet et al., Mol. Gen. Genet. 198:35–41 (1984)). These plasmids could not be stably introduced into tylosin production strains of *S. fradiae*. Stable maintenance without antibiotic selection and very high transformation frequencies are the key advantages of an integrating plasmid vector comprising the site-specific integration functions of φC31.

The vector comprising cloned tylosin biosynthetic genes can also be used to increase the tylosin production of *S. fradiae* mutant strains such as GS15 (tylF mutant; NRRL 18058) and GS16 (tylE mutant; available from the American Type Culture Collection, Rockville, MD 20852 under accession number ATCC 31664). The aforementioned plasmids pSKC50 and pSKC51 comprise the tylE and tylF genes. These plasmids can be transformed into the *S. fradiae* mutant strains. The resulting transformants will produce increased yields of tylosin and be stably maintained.

Thus, an important aspect of the present invention is to provide a method for increasing the antibiotic-producing or antibiotic precursor-producing ability of an antibiotic-producing or antibiotic precursor-producing microorganism, said method comprising 1) transforming a microorganism that produces an antibiotic or an antibiotic precursor by means of an antibiotic biosynthetic pathway with an integrating vector comprising a DNA sequence which comprises the site-specific integrating functions of phage φC31, said vector also comprising an antibiotic biosynthetic gene that codes for an enzyme or other gene product that is rate-limiting in said biosynthetic pathway; and 2) culturing said microorganism transformed with said vector under conditions suitable for cell growth, expression of said antibiotic biosynthetic gene, and production of antibiotic or an antibiotic precursor, subject to the limitation that said antibiotic biosynthetic gene selected in step (1) provides for an increase in the antibiotic-producing or antibiotic precursor-producing ability of said microorganism.

Illustrative tylosin biosynthetic genes that can be used for purposes of the present invention include, for example, the tylA, tylB, tylC, tylD, tylE, tylF, tylG, tylH, tylI, tylJ, tylK, tylL, and tylM, genes. Of this group, the tylF gene is preferred, because the macrocin O-methyltransferase enzyme encoded thereby appears to be rate-limiting in the tylosin biosynthetic pathway of most tylosin-producing strains. Macrocin accumulates to unacceptable levels under conditions of optimum fermentation of *Streptomyces fradiae* because of the rate-limiting step catalyzed by the tylF gene product. The tylF enzyme catalyzes the conversion of macrocin to tylosin. Overproduction of the tylF gene product, macrocin O-methyltransferase, results in the more efficient operation of the tylosin biosynthetic pathway as indicated by increased antibiotic yield and lower cost of fermentation.

Streptomyces strains can be cultured in a number of ways using any of several different media. Carbohydrate sources that are preferred in a culture medium include, for example, molasses, glucose, dextran, and glycerol, and nitrogen sources include, for example, soy flour, amino acid mixtures, and peptones. Nutrient inorganic salts are also incorporated into the medium and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium. Streptomyces strains are grown under aerobic culture conditions over a relatively wide pH range of about 6 to 8 at temperatures ranging from about 25° to 37° C. At temperatures of about 34°–37° C., antibiotic production may cease.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pKC796

Plasmid pKC796 (FIG. 1) can be obtained from the Northern Regional Research Center (NRRL), Peoria, IL 61604, in *E. coli* K12 DH5α under the accession number NRRL B-18477. The lyophils of *E. coli* K12 DH5α/pKC796 were plated onto L-agar plates (10 g of tryptone, 10 g of NaCl, 5 g of yeast extract, and 15 g of agar per liter) containing 100 μg/ml apramycin to obtain a single colony isolate of the strain. This colony was used to inoculate about 500 ml of L broth (L agar without agar) containing 100 μg/ml apramycin, and the resulting culture was incubated at 30° C. with aeration until the cells reached stationary phase.

The cells were centrifuged at 8000 rpm for 10 minutes. After the supernatant was decanted, the cells were resuspended in 7 ml of 25% sucrose, 50 mM Tris.HCl, pH 8.0. Freshly prepared lysozyme (0.25 ml of a 5 mg/ml solution) was added to the solution, along with 0.4 ml of 0.5 M EDTA (pH 8), and 0.05 ml of 5 mg/ml RNase A. The mixture was incubated for 15 minutes at 37° C. To this 0.75 ml of Triton lytic mix (150 mM Tris.HCl, pH 8.0, 3% Triton X-100 ®, 200 mM EDTA) was added, mixed, and incubated for 15 minutes on ice. If lysis was not complete, it was further incubated for about 5 minutes at 37° C. The mixture was centrifuged at 20,000 rpm for 40 minutes. The supernatant was removed and retained. A CsCl gradient (density of 1.55) was made by adding 28.65 g of CsCl to 31.2 ml of DNA solution. The gradient solution was mixed to dissolve and transferred to large ultracentrifuge tubes. The tubes were filled with ~0.6 ml of ethidium bromide (10 mg/ml), sealed and mixed.

The gradient was established by centrifugation at 49,000 rpm for 18 hours. The lower band of plasmid DNA as visualized with long-wave UV light was collected. The ethidium bromide was removed by extracting 4 to 5 times with isoamyl alcohol. The DNA solution was dialyzed against 2 liters of TE buffer (10 mM Tris.HCl, pH 8.0, 1 mM EDTA) and after 2 hours was replaced with fresh TE. The dialyzed solution was extracted twice with phenol and twice with chloroform:isoamyl alcohol (24:1). The DNA was ethanol precipitated by adding one-tenth volume of 3 M sodium acetate and 3 volumes of ethanol. The DNA was collected by centrifugation for 10 minutes at 10,000 rpm, washed with 70% ethanol and then 100% ethanol, dried and dissolved in about 250 μl of sterile TE. The concentration and purity was estimated by measuring optical density at 260 and 280 nm. A restriction site and function map of pKC796 is presented in FIG. 1 of the accompanying drawings.

EXAMPLE 2

Construction of Plasmid pOJ242 and pOJ243

A. Isolation of Plasmid pOJ171

Plasmid pOJ171 can be obtained from the NRRL in *E. coli* K12 SF8 under the accession number NRRL B-18169. Plasmid pOJ171 is a source of the carE gene. The lyophils of *E. coli* K12 SF8/pOJ171 are plated onto L-agar plates containing 100 μg/ml apramycin to obtain a single colony isolate of the strain. This colony is used to inoculate about 500 ml of L broth containing 100 μg/ml apramycin and the resulting culture is incubated at 37° C. with aeration until the cells reach stationary phase.

Plasmid DNA is obtained from the cells to use in construction of plasmids pOJ242 and pOJ243 in substantial accordance with the procedure set forth in Example 1, above. A restriction site and function map of plasmid pOJ171 is presented in FIG. 2 of the accompanying drawings.

B. Final Construction of Plasmids pOJ242 and pOJ243

Plasmids pOJ242 and pOJ243 are vectors that comprise the carE gene. The plasmids can be constructed in the following manner. About 10 μg (10 μl) of plasmid pKC796 DNA is added to 2 μl of 10X BamHI buffer (60 mM Tris-HCl, pH 7.9; 1.5 M NaCl; and 60 mM MgCl$_2$), 6 μl of H$_2$O, and 2 μl (~40 units; unit definitions herein correspond to those of New England Biolabs (NEB), 32 Tozer Road, Beverly, MA 01915-9990, unless otherwise indicated) of restriction enzyme BamHI. The resulting reaction is incubated at 37° C. for two hours. The BamHI-digested plasmid pKC796 DNA is extracted and then collected by adjusting the sodium acetate (NaOAc) concentration of the reaction mixture to 0.30 M, adding 2.5 volumes of ethanol, chilling the reaction mixture to 31 70° C., and centrifuging to pellet the precipitated DNA. pellet of BamHI-digested plasmid pKC796 DNA is resuspended in 10 μl of TE buffer.

About 20 μg of plasmid pOJ171 in 10 μl of TE buffer are added to 75 μl of H$_2$O, 10 μl of 10X BamHI buffer (60 M Tris-HCl, pH 7.9; 1.5 M NaCl; and 60 mM MgCl$_2$), and 5 μl (~100 units) of restriction enzyme BamHI. The resulting reaction is incubated at 37° C. for 2 hours. The reaction mixture is extracted and the DNA collected as described above. The DNA pellet is dissolved in ~10 μl of TE buffer. The DNA is electrophoresed on a low-melting agarose gel (BioRad, 2200 Wright Ave., Richmond, GA, 94804) in substantial accordance with the procedure in Maniatis et al., 1982, *Molecular Cloning* (Cold Spring Harbor Laboratory).

The gel is prepared by heating 100 ml of 0.8% low-melting agarose in IX TAE buffer (40 mM Trisacetate, pH 7.5, 2 mM EDTA). The mixture is cooled to 37° C. and the gel is run at 4° C. Two μl of loadingbuffer (0.25% bromphenol blue, 0.25% xylene cyanol, 30% glycerol in H$_2$O) are added to the DNA sample. The sample is loaded onto the gel. The gel is run at 100 V at 4° C. until the bromphenol blue dye nears the bottom of the gel. The gel is stained with 0.5 μg/ml ethidium bromide and the desired ~2.4 kb BamHI band is detected by long wave UV fluorescence and excised. To the gel piece is added 5 volumes of 20 mM Tris-HCl (pH 8.0) and 1 mM EDTA. The gel is melted at 65° C. for 5 minutes. The sample is extracted with an equal volume of phenol. The sample is centrifuged, the aqueous layer recovered and reextracted, and the DNA collected as described above. The DNA pellet is dissolved in 10 μl of TE buffer and contains ~0.5 μg of the desired ~2.4 kb BamHI restriction fragment of plasmid pOJ171.

The BamHI-digested plasmid pKC796 DNA (1 μl) is added to 10 μl (~0.5 μg) of the BamHI restriction fragment from pOJ171, 2 μl of 10X ligase buffer (660 mM Tris-HCl, pH 8.0; 66 mM MgCl$_2$; 10 mM dithiothreitol (DTT); and 10 mM ATP), and 6 μl of H$_2$O. About 1 μl (~100 units) of T4 DNA ligase is added to the solution of DNA, and the resulting reaction is incubated at 15° C. overnight (~16 hours). The ligated DNA contains the desired plasmids pOJ242 and pOJ243 which differ only in the orientation of the ~2.4 kb BamHI insert fragment; restriction site maps of pOJ242 and pOJ243 are presented in FIGS. 3 and 4 of the accompanying drawings.

The BamHI site on plasmid pKC796 resides within a multiple cloning site that itself forms part of the DNA sequence encoding the lacZ α-fragment. Expression of the lacZ α-fragment in an *E. coli* 66 M15 strain, such as *E. coli* K12 DH5α, restores the strain's ability to produce a functional β-galactosidase enzyme. Thus, plasmid pKC796 can restore β-galactosidase activity to the *E. coli* K12 DH5α strain. However, insertion of DNA into a restriction site of the polylinker on plasmid pKC796, as occurs in the construction of plasmids pOJ242 and pOJ243, disrupts the lacZ α-fragment coding sequence and concomitantly destroys the ability of the plasmid pKC796 derivative to complement the 66 M15 mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pKC796 and those containing a plasmid pKC796 derivative, such as plasmid pOJ242 or pOJ243.

Frozen competent DH5α cells (Bethesda Research Laboratories, Inc. (BRL), P.O. Box 6009, Gaithersburg, MD, 20877) were transformed as per manufacturer's instructions. The cells were thawed on ice, 100 μl of cells were removed per transformation, and the unused cells were refrozen in a dry ice-ethanol bath. The 100 μl of cells were added to 1 μl of the ligation reaction which had been diluted 5 fold with water. The cells were incubated on ice for 30 minutes, heat shocked at 42° C. for 2 minutes, and returned to ice for 2–5 minutes. One ml of SOC medium was added and the cells were incubated for one hour at 37° C. with shaking. SOC medium is 2% (w/v) tryptone, 0.5% (w/v) yeast extract, 20 mM glucose, 10 mM NaCl, 2.5 mM KCl, 10 mM MgCl$_2$, and 10 mM MgSO$_4$.

Aliquots of the transformation mixture were plated on L-agar plates containing 100 μg apramycin/ml, 40 μg X-gal/ml, and 40 μg IPTG/ml. IPTG serves to derepress the lac promoter present on plasmid pKC796. The plates were incubated at 37° C. overnight. Colonies that contain a plasmid without an insert, such as *E. coli* K12 DH5α/pKC796, appear blue on these plates. Colonies that contain a plasmid with an insert, such as *E. coli* K12 DH5α/pOJ242, are white. Several apramycin-resistant, white colonies were selected and then screened by resriction enzyme analysis of their plasmid DNA. Plasmid DNA was obtained from the *E. coli* K12 DH5α/pOJ242 and pOJ243 transformants in accordance withy the procedure for isolating plasmid DNA. The plasmid pOJ242 and pOJ243 DNAs were used to transform *Streptomyces ambofaciens* strain 2281 as described in Example 3, below. The publicly available *S. ambofaciens* strains NRRL 2420 or NRRL 15263 would function equally well.

EXAMPLE 3

Transformation of Streptomyces

A. List of Solutions

The following solutions are referred to throughout the Examples and are presented here for clarity.

| Ingredient | Amount |
| --- | --- |
| 1. P Medium (~100 ml): | |
| Sucrose | 10.3 g |
| K$_2$SO$_4$ | 0.025 g |
| Trace element solution (see #3) | 0.2 ml |
| MgCl$_2$.6H$_2$O | 0.203 g |
| Water | 80 ml |
| After autoclaving add: | |
| KH$_2$PO$_4$ (0.5%) | 1 ml |
| CaCl$_2$.2H$_2$O (3.68%) | 10 ml |
| (N-tris-(hydroxymethyl)-methyl-2-aminoethane sulphonic acid), "TES" buffer, 0.25 M, pH = 7.2 | 10 ml |
| 2. Trace element solution (~1 L): | |
| ZnCl$_2$ | 40 mg |
| FeCl$_3$.6H$_2$O | 200 mg |
| CuCl$_2$.2H$_2$O | 10 mg |
| MnCl$_2$.4H$_2$O | 10 mg |
| Na$_2$B$_4$O$_7$.10H$_2$O | 10 mg |
| (NH$_4$)$_6$Mo$_7$O$_{24}$.4H$_2$O | 10 mg |
| H$_2$O | 1 L |
| 3. Modified R2 Regeneration Medium (~1 L): | |
| Sucrose | 103 g |
| K$_2$SO$_4$ | 0.25 g |
| Trace element solution | 2 ml |
| MgCl$_2$.6H$_2$O | 10.12 g |
| glucose | 10 g |
| L-asparagine.1H$_2$O | 2.0 g |
| casamino acids | 0.1 g |
| Agar | 22 g |
| Water | to 700 ml |
| The pH is adjusted to pH 7.2 before autoclaving. | |
| After autoclaving, add: | |
| KH$_2$PO$_4$ (0.05 g/100 ml) | 100 ml |
| CaCl$_2$ (2.22 g/100 ml) | 100 ml |
| TES Buffer (5.73 g/100 ml, pH = 7.2) | 100 ml |
| 4. Soft Nutrient Agar (SNA, ~1 L): | |
| Difco Bacto Nutrient Broth | 8 g |
| Agar | 5 g |
| 5. R2YE medium is R2 medium with 20 ml of 25% yeast extract added per liter. | |
| 6. Yeast Extract - Malt Extract (YEME, ~1 L): | |
| Yeast extract | 3 g |
| Peptone | 5 g |
| Malt extract | 3 g |
| Glucose | 10 g |
| 7. YEME + 34% Sucrose Liquid Complete Media is YEME with 340 g/L of sucrose. | |
| 8. YMX Medium (~1 L): | |
| Yeast extract | 3 g |
| Malt extract | 3 g |
| Glucose | 2 g |
| Agar | 20 g |
| 9. YMX Agar is 0.3% yeast extract, 0.3% malt extract, 0.2% dextrose, and 2.0% agar. | |
| 10. Tylosin Fermentation Medium | |
| Beet Molasses | 2% |
| Corn Meal | 1.5% |
| Fish Meal | 0.9% |
| Corn Gluten | 0.9% |
| Sodium Chloride | 0.1% |
| Ammonium Phosphate (dibasic) | 0.04% |
| Calcium Carbonate | 0.2% |
| Crude Soybean Oil | 3% |
| The pH of this medium was adjusted to 7.1 with 1 N NaOH. | |
| 11. ASI Medium (~1L deionized H$_2$O) | |
| Yeast Extract | 1 g |
| L-alanine | 0.2 g |
| L-arginine (free base) | 0.2 g |
| L-asparagine | 0.5 g |
| Soluble Starch | 5 g |
| Sodium Chloride | 2.5 g |
| Sodium Sulfate | 10 g |
| Meer Agar | 20 g |
| 12. Spiramycin Fermentation Medium (~1L) | |
| Yeast Extract | 10 g |
| KCl | 2.5 g |
| MgSO$_4$ | 0.1 g |
| KH$_2$PO$_4$ | 10 g |

-continued

| Ingredient | Amount |
| --- | --- |
| FeCl₂ | 0.03 g |
| ZnCl₂ | 0.03 g |
| MnCl₂ | 0.01 g |
| Ammonium Molybdate | 0.005 g |
| These ingredients were dissolved in 800 ml of water and autoclaved. To this was added sterile potato dextrin (15 g) and glucose (10 g) in 200 ml of water. | |
| 13. Modified R2 Soft Agar Overlays | |
| Sucrose | 51.5 g |
| MgCl₂.H₂O | 5.06 g |
| CaCl₂ | 1.11 g |
| 0.25M TES (pH 7.2) | 50 ml |

These ingredients are dissolved in deionized water such that the final volume is 500 ml. The mixture is steamed to melt the agar, decanted into 4 ml aliquots, and autoclaved prior to use.

B. Transformation of *S. fradiae*

A culture of *Streptomyces fradiae* was inoculated into 20 ml of trypticase-soya broth (TSB) and incubated in a water-bath incubator at 29° C. at 260 rpm overnight (about 16 hours). The culture was homogenized using a homogenizing vessel (Thomas Scientific, Swedesboro, NJ) and a T-Line laboratory stirrer and then fragmented using a Sonifier cell disruptor (Heat Systems Ultrasonics, Inc.) for 7 seconds at 76 Watts. Four ml of the homogenized, fragmented culture were inoculated into 20 ml of TSB (BBL) containing 0.3% weight by volume glycine, and the culture was again incubated overnight at 29° C. The following morning, the culture was homogenized and recultured as described above. After this third overnight incubation, the culture was homogenized, collected, and then washed twice with P media.

The cell pellet was resuspended in 15 ml of P media containing 1 mg/ml lysozyme (Calbiochem, La Jolla, CA 92037) and then incubated at room temperature for about one-and-one-half hours to form protoplasts. The protoplasts were gently collected by centrifugation, washed twice with P media, resuspended in 2 ml of P media, and incubated on ice until use. About 1 µg of plasmid DNA was added to about 50 µl of 1 mg/ml heparin sulfate (Sigma) and incubated on ice for about 10 minutes. Much less plasmid DNA, about 5-100 nanograms, can be used to transform *Streptomyces fradiae* if prepared from a *S. fradiae* host. The procedure for isolating Streptomyces plasmid DNA is described in Hopwood et al., 1985, *Genetic Manipulation of Streptomyces: A Laboratory Manual* (John Innes Foundation, Norwich, England). The DNA/heparin solution was first added to about 200 µl of protoplasts, and about 0.9 ml of a solution composed of 55% PEG 1000 (Sigma) in P medium was then added to the DNA/protoplast mixture, and the resulting mixture was gently mixed at room temperature.

The mixture was plated in varying aliquots onto R2 plates using 4 ml of soft-R2-agar overlays. After the transformed protoplasts had been plated, the plates were incubated at 29° C. for 24 hours, and then, 4 ml of soft-R2 agar containing 25 µl of 50 mg/ml thiostrepton (E. R. Squibb, Princeton, NJ 08540) were spread over the protoplasts. Incubation of the plates at 29° C. was continued until regeneration was complete, usually a period of about 7-14 days, to select for the desired *S. fradiae* transformants.

C. Transformation of Streptomyces (except for *S. fradiae*)

One half ml of a fully grown overnight culture of Streptomyces, homogenized and sonicated, was used to inoculate 9.5 mls of TSB plus 0.5% glycine. The culture was incubated at 30° C. for 24 hours. After homogenization with a tissue grinder, 0.5 ml of homogenate was used to inoculate 9.5 ml of fresh TSB supplemented with 0.5% glycine. The culture was incubated at 30° C. for 24 hours. The culture was homogenized and transferred to a 50 ml sterile polystyrene centrifuge tube. The cells were pelleted by centrifugation for 10 minutes at 3500 rpm, washed with 10 ml of P medium and resuspended in 10 ml of P medium with 1 mg/ml lysozyme, then incubated at room temperature for 15-30 minutes. Protoplast formation was monitored by examining small samples under a phase-contrast microscope. Protoplasts are spherical.

The protoplasts were centrifuged as before and washed once in P medium. The cells were resuspended in 10 ml of P medium and 150 µl of protoplasts for each transformation were placed in a 1.5 ml Eppendor® tube. Up to 10 µl of DNA in TE buffer were added with gentle mixing. One hundred µl of 50% polyethylene glycol 1000 in P medium were added immediately. Each transformation mix was split into two tubes of 4 ml of modified R2 top agar and poured onto dried modified R2 plates. The plates were incubated at 30° C. for 24 hours. The plates were then overlaid with modified R2 top agar containing sufficient apramycin for a final plate concentration of 50 µg/ml. The plates were incubated at 30° C. and transformants appeared 2-3 days later. The transformants were analyzed for the presence of integrated plasmid DNA by Southern analysis in substantial accordance with the procedure in Maniatis et al., 1982, *Molecular Cloning* (Cold Spring Harbor Laboratory).

EXAMPLE 4

Assay of Antibiotic Production by Streptomyces

A. Plate-Plug Assay

To determine whether a strain produced antibiotic, *Streptomyces ambofaciens* and *S. fradiae* transformants or parent controls were patched from the R2-agar regeneration plates to AS1 plates and incubated at 30° C. for 2-3 days (5-7 days for *S. fradiae*) until the colonies were 5-10 millimeters in diameter. In order to test the production of isovaleryl spiramycin by *S. ambofaciens* transformed with pOJ242 or pOJ243, the strains were grown on AS1 plates containing A) 50 µg/ml apramycin; B) 50 µg/ml apramycin and 100 µg/ml leucine; C) no additions or D) 100 µg/ml leucine. The colonies were then plugged with a sterile transfer tube (Spectrum Medical Industrial, Inc., Los Angeles, CA 90054) and transferred to trypticase soy agar (TSA) plates, which had been previously overlayed with soft-agar nutrient broth (Difco Laboratories, Detroit, MI 48232) containing *Micrococcus luteus* X160 (ATCC 9341). The plates were incubated at 37° C. for 16-24 hours. *Micrococcus luteus* is sensitive to tylosin and spiramycin and resistant to apramycin. Consequently, *M. luteus* cannot grow around a plug which contains Streptomyces that are producing tylosin, spiramycin, or isovaleryl spiramycin. A zone of inhibition indicates the presence of antibiotic.

B. Bioautography

The agar from an entire plate containing the organism of interest which has been grown for the appropriate time at 30° C. was macerated in 10 ml of 1 M Tris-HCl pH 8.0 in a 50 ml polypropylene centrifuge tube. Ten ml of ethyl acetate were added and the mixture was shaken vigorously several times over a period of 1-2 hours at room temperature. The layers were separated in a table-top centrifuge and the top ethyl acetate layer was recovered and evaporated to dryness in a dish. The residue was dissolved in 1 ml of methanol. Approximately 1-20 μl of the methanol extract were applied to a TLC plate and dried. Separation was carried out on a thin-layer chromatography plate (Merck, P.O. Box 2000, Rahway, New Jersey 07065, pre-coated silica gel #60 F-254) next to a tylosin or spiramycin standard. When agar plugs were being assayed, the plugs were left on the plate for a time sufficient for diffusion to occur; then, the plate was subjected to ascending liquid chromatography in 95:5:5 ethylacetate:diethylamine:methanol. The developed chromatograms were dried thoroughly in a fume hood for at least two hours. The chromatograms were then placed face down on *Micrococcus luteus* X160-seeded TSA plates for ~15 minutes. The chromatograms were removed from the plates, and the plates were incubated at 37° for 16-24 hours. Zones of inhibition were compared with a tylosin or spiramycin standard.

The *S. ambofaciens* strain containing integrated plasmid pKC796 alone continued to produce spiramycin as demonstrated by isocratic HPLC analysis. Methanol extracts were run on a DuPont Bondapak C18 column (DuPont Co., Instrument Products, Biomedical Division, Newtown, CT 06470) in a mobile phase composed of 80% acetonitrile and 20% 0.1% ammonium bicarbonate, pH=7. The experimental samples were compared against standards of spiramycin esters. Elution times are given in the following table. The structures of spiramycin I, II and III can be found in Omura and Nakagawa, J. Antibiot. 28:401-433 (1975).

TABLE XI

| Product | Elution Time (Minutes) |
| --- | --- |
| With carE | |
| Isovaleryl spiramycin II | 26.5 |
| Isovaleryl spiramycin III | 32.0 |
| Butyryl spiramycin II | 23.0 |
| Spiramycin standards | |
| Spiramycin I | 15.3 |
| Spiramycin II | 16.5 |
| Spiramycin III | 19.5 |

The *S. ambofaciens* strain integrated with plasmids pOJ242 or pOJ243 produced the novel hybrid antibiotics isovaleryl and butyryl spiramycin. The results are shown below.

In the following table, A stands for 50 μg/ml apramycin and L stands for 100 μg/ml leucine. The results are expressed in terms of percent conversion of spiramycin to isovaleryl and butyryl spiramycin. The "Total Spiramycin+Ester" column is an indication of the overall antibiotic production rate of the transformant. Therefore, a transformant with a high value in that column would be making more isovaleryl and butyryl spiramycin than a transformant with an identical "% conversion" value and a lower "Total Spiramycin+Ester" value. Plasmid pOJ224 is an autonomously replicating vector, unrelated to pKC796, but which comprises the identical carE-comprising fragment as pOJ242 and pOJ243.

TABLE XII

| Growth Conditions and Vector | % Conversion | Total Spiramycin + Ester (μg/sample) |
| --- | --- | --- |
| A+L- | | |
| pKC796 | 0 | 2.0 |
| pOJ242 | 66 | 1.9 |
| pOJ243 | 68 | 1.8 |
| pOJ224 | 55 | 0.6 |
| A+L+ | | |
| pKC796 | 0 | 1.8 |
| pOJ242 | 78 | 1.9 |
| pOJ243 | 80 | 1.9 |
| pOJ224 | 74 | 0.4 |
| A-L- | | |
| pKC796 | 0 | 2.1 |
| pOJ242 | 62 | 1.9 |
| pOJ243 | 60 | 2.3 |
| pOJ224 | 26 | 0.9 |
| A-L+ | | |
| pKC796 | 0 | 3.7 |
| pOJ242 | 77 | 2.7 |
| pOJ243 | 77 | 3.3 |
| pOJ224 | 60 | 0.6 |

Several conclusions can be drawn from this data. The most important is that a large increase in overall production is obtained with an integrating vector in lieu of an autonomously replicating plasmid. The presence of such a plasmid in a cell diverts many of the cell's resources toward maintaining the plasmid. In turn, the antibiotic production capabilities of the cell may be reduced. The increase in antibiotic production is but one of the many advantages of pKC796 as a vector for maintaining cloned genes. Another observation based on this data is that the carE gene, in either orientation, causes the conversion of large amounts of spiramycin to isovaleryl and butyryl spiramycin. The conversion is augmented by the presence of leucine in the growth medium. Finally, it can be seen that antibiotic selection is not a requirement for maintenance of the carE phenotype with the integrating vector. This represents another significant advantage of pKC796.

EXAMPLE 5

Construction of Plasmids pSKC50 and pSKC51

A. Isolation of Plasmid pHJL280

Figure 5:
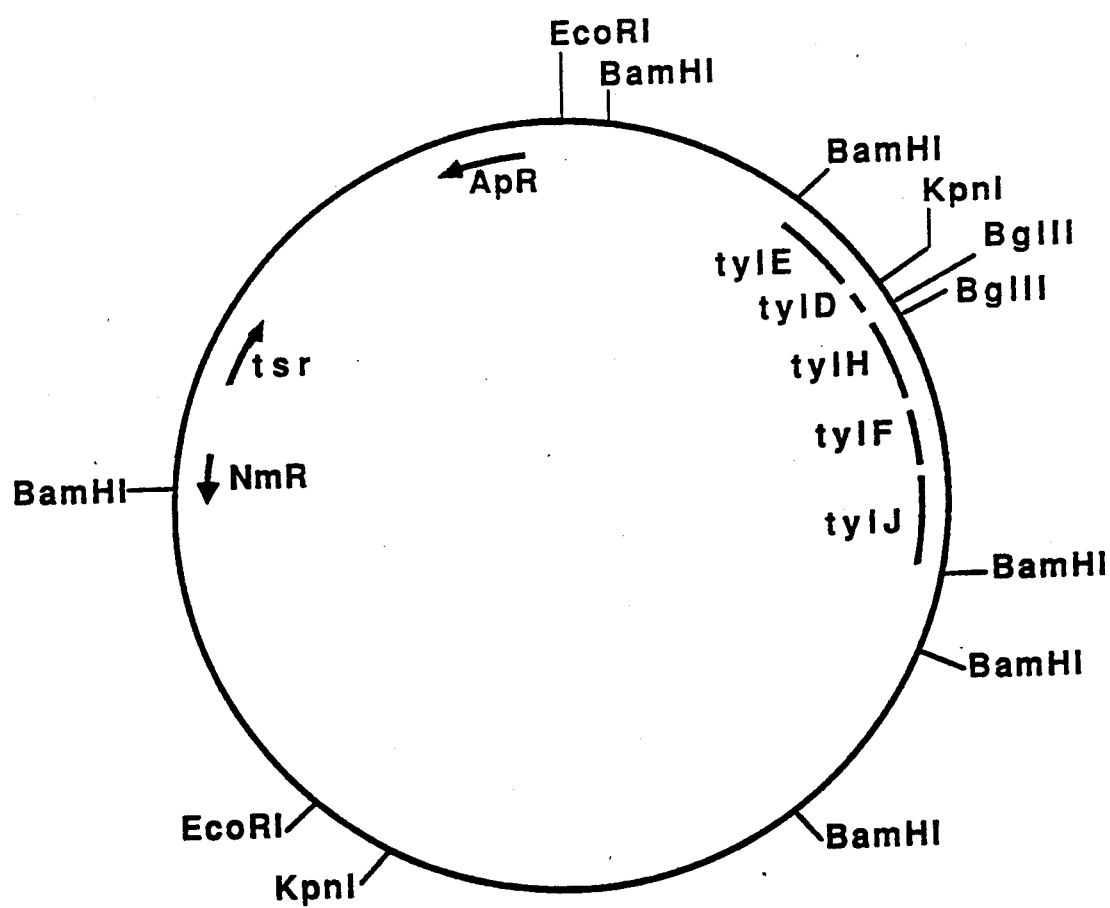
FIG. 5 - Restriction Site and Function Map of Plasmid pHJL280.

Plasmid pHJL280 was isolated from *E. coli* K12 HB101 on deposit with the NRRL under accession number NRRL B-18043. A restriction site and function map of pHJL280 is presented in FIG. 5. The plasmid serves as the source of the tylosin biosynthetic genes tylE, tylD, tylF, tylH and tylJ. These genes are present on an ~6 kb BamHI fragment of pHJL280.

The plasmid was isolated in substantial accordance with Example 1 except that 100 μg/ml ampicillin was used in the medium rather than apramycin.

B. Final Construction of Plasmids pSKC50 and pSKC51

Figure 6:
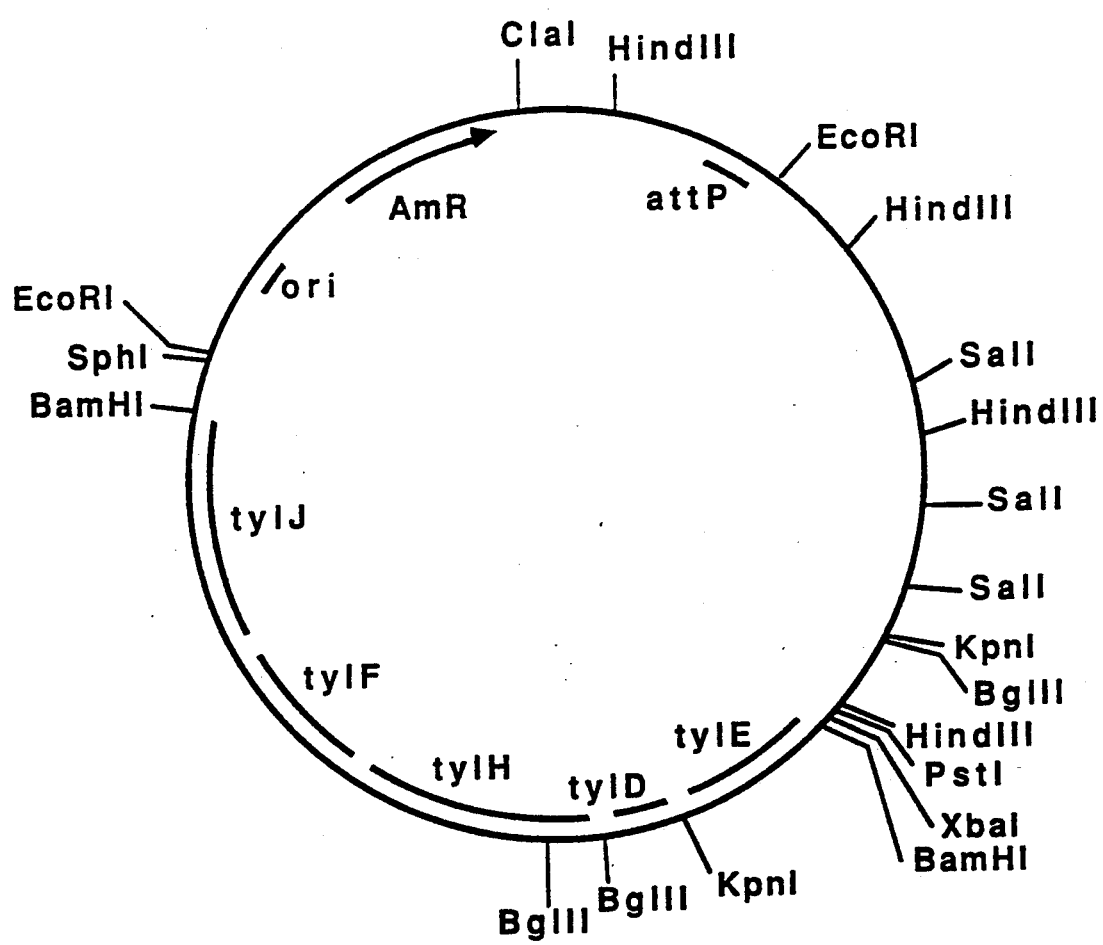
FIG. 6 - Restriction Site and Function Map of Plasmid pSKC50.
Figure 7:
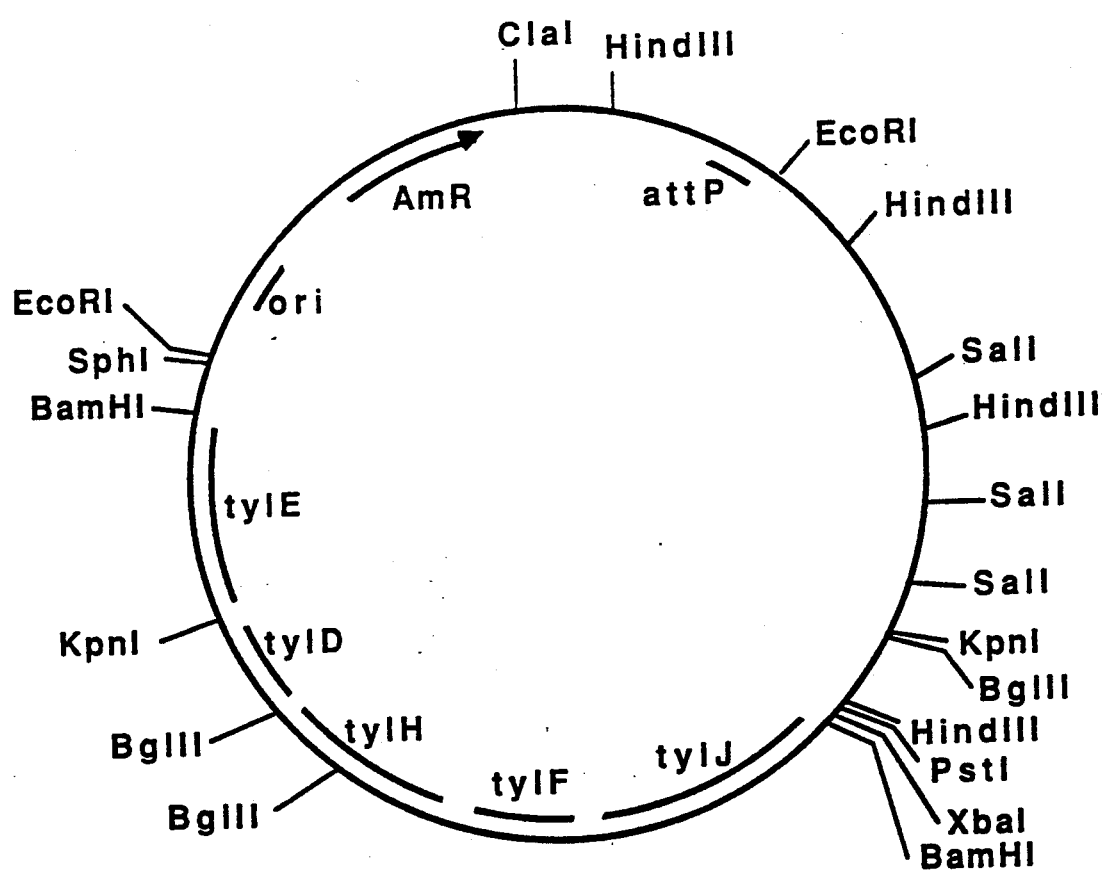
FIG. 7 - Restriction Site and Function Map of Plasmid pSKC51.

Plasmids pSKC50 and pSKC51 are vectors that were used to integrate extra copies of the tylosin biosynthetic genes into the *Streptomyces fradiae* chromosome. The plasmids were constructed in the following manner. About 10 μg (10 μl) of plasmid pKC796 DNA were digested with restriction enzyme BamHI as per Example 2B. About 20 μg of plasmid pHJL280 were digested with BamHI and the ~6 kb DNA fragment isolated in substantial accordance with Example 2B. The BamHI-digested pKC796 and ~6 kb fragment of pHJL280 were then ligated and transformed into *E. coli* dh5α in substantial accordance with Example 2B. The resulting plasmids were pSKC50 and pSKC51, differing only by the orientation of the ~6 kb BamHI fragment (See FIGS. 6 and 7). The plasmids were then transformed as described ion Example 3, above, into *S. fradiae* T1405. The samples were then assayed for tylosin production in substantial accordance with Example 4, above.

The results with experiments utilizing the *S. fradiae* production strain were as follows. The results are expressed as percent of tylosin produced as compared to the control T1405 production strain (with no vector integrated).

TABLE XII

| Strain | Tylosin Produced % of Control | |
|---|---|---|
| | Experiment 1 | Experiment 2 |
| T1405 | 100 | 100 |
| T1405/pKC796 | not done | 98 |
| T1405/pSKC50 or pSKC51 | 133 | 136 |

The results indicate that integrating extra copies of the tylosin biosynthetic genes increases tylosin production by a substantial amount.

EXAMPLE 6

Transformation of tyl Mutant Strains GS15 and GS16 with Plasmid pKC796, pSKC50 and pSKC51

*Streptomyces fradiae* strains GS15 and GS16 are grown, protoplasted and transformed with pSKC50 and pSKC51 as described in Example 3. Apramycin resistant transformants containing pSKC50 or pSKC51 are grown in TS broth plus 50 μg/ml of apramycin for about 48 hours or until the cultures reach stationary phase. One-half ml of each culture is inoculated into 7 ml of tylosin fermentation medium (Example 3) and the culture is incubated at 29° C. for seven days with rapid agitation. Five ml of methanol are added to each culture. After mixing by hand shaking, the methanol diluted fermentation cultures are filtered through Whatman #1 paper. The filtrates are analyzed for the presence of tylosin, macrocin and demethylmacrocin by thin layer chromatography (Baltz and Seno, *Antimicrob. Agents Chemother.* 20:214–225 (1981)) and HPLC (Kennedy, *J. of Chrom.* 281:288–292 (1983)). The results are compared to those from concurrently run control cultures consisting of GS15 or GS16 without pSKC50 or pSKC51.

We claim:

1. A method for directing integration of a plasmid into a streptomycete genome which comprise the step of introducing into said streptomycete a plasmid comprising a DNA sequence, such DNA sequence containing site-specific integrating functions of phage φC31 subject to the limitation that the plasmid not be capable of directing plaque formation.

2. The method of claim 1, wherein said DNA sequence comprising the site-specific integrating functions of phage φC31 is

```
GAC GTC CCG AAG GCG TGG CGC GGC TTC CCC GTG CCG GAG CAA
TCG CCC TGG GTG GGT TAC ACG ACG CCC CTC TAT GGC CCG TAC
TGA CGG ACA CAC CGA AGC CCC GGC GGC AAC CCT CAG CGG ATG
CCC CGG GGC TTC ACG TTT TCC CAG GTC AGA AGC GGT TTT CGG
GAG TAG TGC CCC AAC TGG GGT AAC CTT TGA GTT CTC TCA GTT
GGG GGC GTA GGG TCG CCG ACA TGA CAC AAG GGG TTG TGA CCG
GGG TGG ACA CGT ACG CGG GTG CTT ACG ACC GTC AGT CGC GCG
AGC GCG AGA ATT CGA GCG CAG CAA GCC CAG CGA CAC AGC GTA
GCG CCA ACG AAG ACA AGG CGG CCG ACC TTC AGC GCG AAG TCG
AGC GCG ACG GGG GCC GGT TCA GGT TCG TCG GGC ATT TCA GCG
AAG CGC CGG GCA CGT CGG CGT TCG GGA CGG CGG AGC GCC CGG
AGT TCG AAC GCA TCC TGA ACG AAT GCC GCG CCG GGC GGC TCA
ACA TGA TCA TTG TCT ATG ACG TGT CGC GCT TCT CGC GCC TGA
AGG TCA TGG ACG CGA TTC GGA TTG TCT CGG AAT TGC TCG CCC
TGG GCG TGA CGA TTG TTT CCA CTC AGG AAG GCG TCT TCC GGC
AGG GAA ACG TCA TGG ACC TGA TTC ACC TGA TTA TGC GGC TCG
ACG CGT CGC ACA AAG AAT CTT CGC TGA AGT CGG CGA AGA TTC
TCG ACA CGA AGA ACC TTC AGC GCG AAT TGG GCG GGT ACG TCG
GCG GGA AGG CGC CTT ACG GCT TCG AGC TTG TTT CGG AGA CGA
AGG AGA TCA CGC GCA ACG GCC GAA TGG TCA ATG TCG TCA TCA
ACA AGC TTG CGC ACT CGA CCA CTC CCC TTA CCG GAC CCT TCG
AGT TCG AGC CCG ACG TAA TCC GGT GGT GGT GGC GTG AGA TCA
AGA CGC ACA AAC ACC TTC CCT TCA AGC CGG GCA GTC AAG CCG
CCA TTC ACC CGG GCA GCA TCA CGG GGC TTT GTA AGC GCA TGG
ACG CTG ACG CCG TGC CGA CCC GGG GCG AGA CGA TTG GGA AGA
AGA CCG CTT CAA GCG CCT GGG ACC CGG CAA CCG TTA TGC GAA
TCC TTC GGG ACC CGC GTA TTG CGG GCT TCG CCG CTG AGG TGA
TCT ACA AGA AGA AGC CGG ACG GCA CGC CGA CCA CGA AGA TTG
AGG GTT ACC GCA TTC AGC GCG ACC CGA TCA CGC TCC GGC CGG
TCG AGC TTG ATT GCG GAC CGA TCA TCG AGC CCG CTG AGT GGT
ATG AGC TTC AGG CGT GGT TGG ACG GCA GGG GGC GCG GCA AGG
GGC TTT CCC GGG GGC AAG CCA TTC TGT CCG CCA TGG ACA AGC
TGT ACT GCG AGT GTG GCG CCG TCA TGA CTT CGA AGC GCG GGG
AAG AAT CGA TCA AGG ACT CTT ACC GCT GCC GTC GCC GGA AGG
TGG TCG ACC CGT CCG CAC CTG GGC AGC ACG AAG GCA CGT GCA
ACG TCA GCA TGG CGG CAC TCG ACA AGT TCG TTG CGG AAC GCA
TCT TCA ACA AGA TCA GGC ACG CCG AAG GCG ACG AAG AGA CGT
TGG CGC TTC TGT GGG AAG CCG CCC GAC GCT TCG GCA AGC · TCA
CTG AGG CGC CTG AGA AGA GCG GCG AAC GGG CGA ACC TTG TTG
CGG AGC GCG CCG ACG CCC TGA ACG CCC TTG AAG AGC TGT ACG
AAG ACC GCG CGG CAG GCG CGT ACG ACG GAC CGT TGG GCA GGA
AGC ACT TCC GGA AGC AAC AGG CAG CGC TGA CGC TCC GGC AGC
```

-continued

| AAG | GGG | CGG | AAG | AGC | GGC | TTG | CCG | AAC | TTG | AAG | CCG | CCG | AAG |
| --- | --- | --- | --- | --- | --- | --- | --- | --- | --- | --- | --- | --- | --- |
| CCC | CGA | AGC | TTC | CCC | TTG | ACC | AAT | GGT | TCC | CCG | AAG | ACG | CCG |
| ACG | CTG | ACC | CGA | CCG | GCC | CTA | AGT | CGT | GGT | GGG | GGC | GCG | CGT |
| CAG | TAG | ACG | ACA | AGC | GCG | TGT | TCG | TCG | GGC | TCT | TCG | TAG | ACA |
| AGA | TCG | TTG | TCA | CGA | AGT | CGA | CTA | CGG | GCA | GGG | GGC | AGG | GAA |
| CGC | CCA | TCG | AGA | AGC | GCG | CTT | CGA | TCA | CGT | GGG | CGA | AGC | CGC |
| CGA | CCG | ACG | ACG | ACG | AAG | ACG | ACG | CCC | AGG | ACG | GCA | CGG | AAG |
| ACG | TAG | CGG | CGT | AGC | GAG | ACA | CCC | GGG | AAG | CCT | | | | wherein A is a deoxyadenyl residue, G is a deoxyguanyl residue, C is a deoxycytidyl residue, and T is a thymidyl residue.

3. The method of claim 1 wherein said plasmid further comprises an *E. coli* origin of replication.

4. The method of claim 1 wherein said plasmid further comprises an antibiotic resistance gene.

5. The method of claim 1 wherein said plasmid further comprises a multiple cloning site.

6. The method of claim 3 wherein said origin of replication is derived from a pUC plasmid.

7. The method of claim 4 wherein said antibiotic resistance gene confers resistance to apramycin.

8. The method of claim 1 wherein said plasmid is pKC796.

9. The method of claim 1 wherein said plasmid further comprises an antibiotic biosynthetic gene.

10. The method of claim 9 wherein said plasmid comprises a tylosin biosynthetic gene.

11. The method of claim 9 wherein said plasmid comprises a carbomycin biosynthetic gene.

12. The method of claim 10 wherein said plasmid is pSKC50.

13. The method of claim 10 wherein said plasmid is pSKC51.

14. The method of claim 11 wherein said plasmid is pOJ242.

15. The method of claim 11 wherein said plasmid is pOJ243.

16. A plasmid selected from the group consisting of pKC796, pOJ242, pOJ243, pSKC50, and pSKC51.

17. The plasmid of claim 16 that is pKC796.

18. The plasmid of claim 16 that is pOJ242.

19. The plasmid of claim 16 that is pOJ243.

20. The plasmid of claim 16 that is pSKC50.

21. The plasmid of claim 16 that is pSKC51.

22. An streptomycete transformed with a plasmid comprising the site-specific integrating functions of phage φC31 subject to the limitation that the plasmid not be capable of directing plaque formation.

23. The streptomycete of claim 22 transformed with a plasmid selected from the group consisting of pKC796, pOJ242, pOJ243, pSKC50, and pSKC51.

24. The streptomycete of claim 23 transformed with plasmid pKC796.

25. The streptomycete of claim 23 transformed with plasmid pOJ242.

26. The streptomycete of claim 23 transformed with plasmid pOJ243.

27. The streptomycete of claim 23 transformed with plasmid pSKC50.

28. The streptomycete of claim 23 transformed with plasmid pSKC51.

* * * * *